United States Patent [19]

Brooker

[11] Patent Number: 4,627,444

[45] Date of Patent: Dec. 9, 1986

[54] DEVICE FOR SAMPLING TISSUES AND FLUIDS FROM BODILY CAVITIES

[75] Inventor: Doris C. Brooker, Eden Prairie, Minn.

[73] Assignee: Regents of the University of Minnesota, Minneapolis, Minn.

[21] Appl. No.: 746,910

[22] Filed: Jun. 20, 1985

[51] Int. Cl.⁴ ............................................. A61B 10/00
[52] U.S. Cl. .................................... 128/758; 128/760
[58] Field of Search .............. 128/130, 304, 749, 758, 128/757, 768; 604/13–16, 18, 35, 54, 55, 319

[56] References Cited

U.S. PATENT DOCUMENTS

| | | | |
|---|---|---|---|
| 2,063,202 | 2/1935 | Spicer | 128/130 |
| 3,568,660 | 3/1971 | Crites et al. | 128/419 |
| 3,889,657 | 6/1975 | Baumgarten | 128/2 |
| 4,166,469 | 10/1979 | Littleford | 128/419 |
| 4,230,123 | 10/1980 | Hawkins, Jr. | 128/658 |
| 4,311,140 | 1/1982 | Bridgman | 128/276 |
| 4,338,952 | 7/1982 | Augros | 128/757 |
| 4,393,879 | 7/1983 | Milgrom | 128/758 |
| 4,396,022 | 8/1983 | Marx | 128/758 |
| 4,457,313 | 7/1984 | Alter | 128/749 |

Primary Examiner—Kyle L. Howell
Assistant Examiner—Randy Citrin
Attorney, Agent, or Firm—Kinney & Lange

[57] ABSTRACT

A device and process for sampling tissue and fluid from bodily cavities comprises an aspirating curette or catheter with at least one notch at its distal end to provide edges for a scraping action sufficient to loosen tissue from the wall of a bodily cavity. The aspirating curette is slidably mounted in and encased by a protective sleeve that has a contamination preventing plug at its outer end. The protective sleeve is shorter than the curette and a removable stop member is provided to initially limit the movement of the protective sleeve toward the base of the curette. When the protective sleeve and curette have been inserted into the bodily cavity the stop is removed, permitting the aspirating curette to be moved outwardly through the protective sleeve, dislodging the plug and exposing the notch in the curette. Fluids may be drawn into the aspirating curette which is then rotated to scrape the cavity wall, and the curette is drawn back into the protective sleeve. The apparatus is then removed from the bodily cavity as a unit with the currette and collected specimen protected from contamination and from oxygen.

16 Claims, 8 Drawing Figures

U.S. Patent Dec. 9, 1986 Sheet 1 of 2 4,627,444
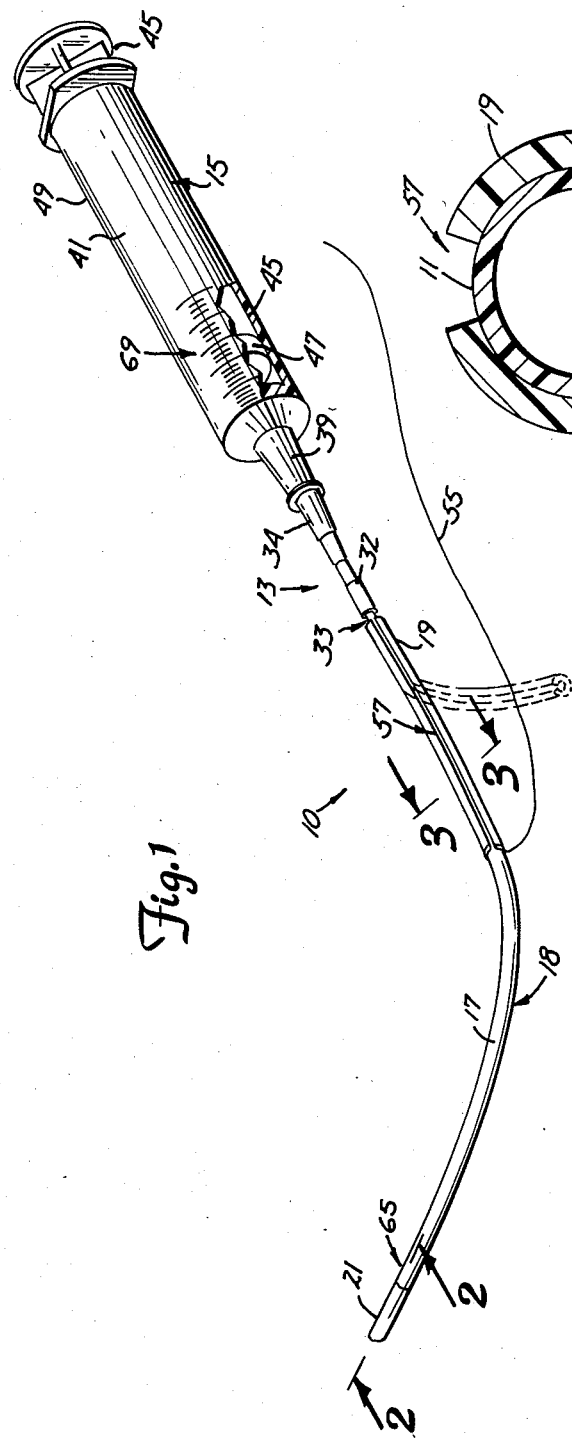
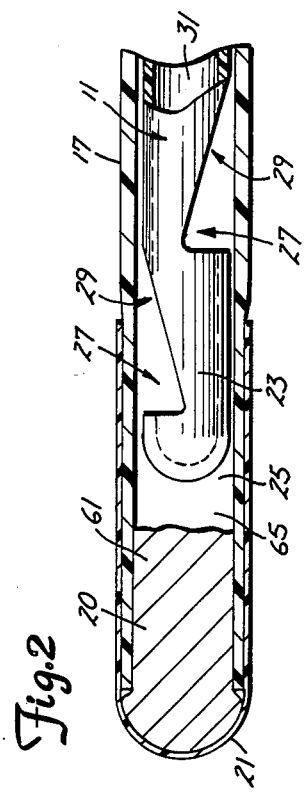
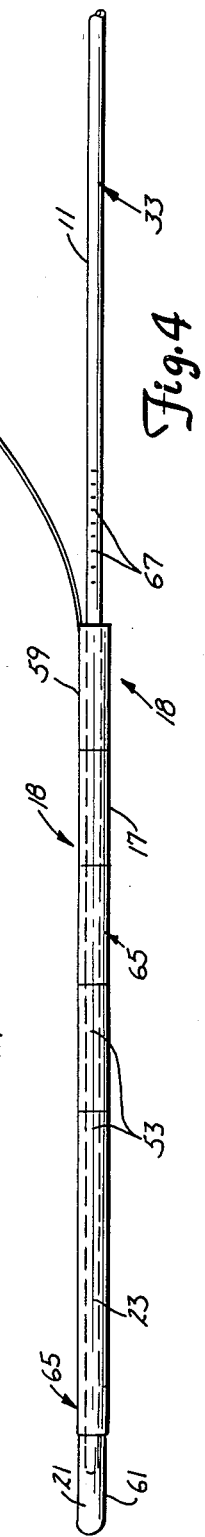

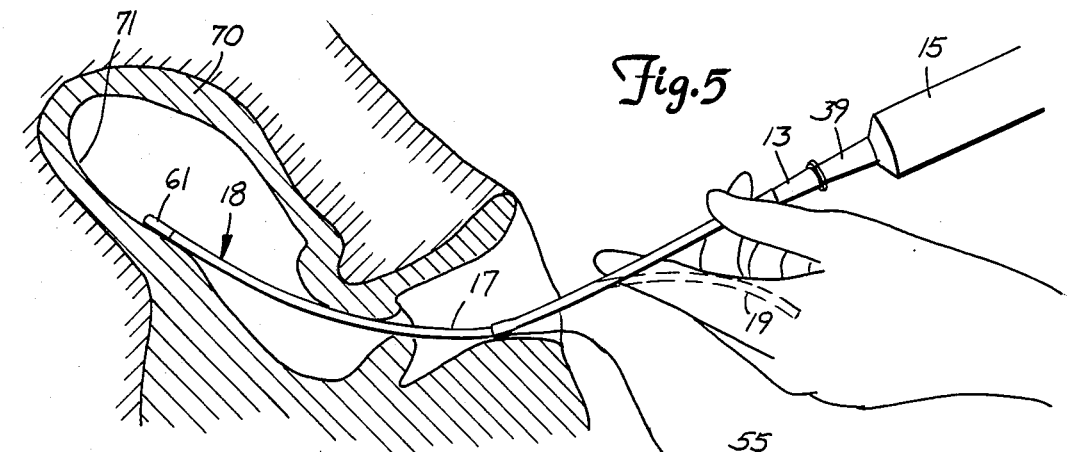
Fig. 5
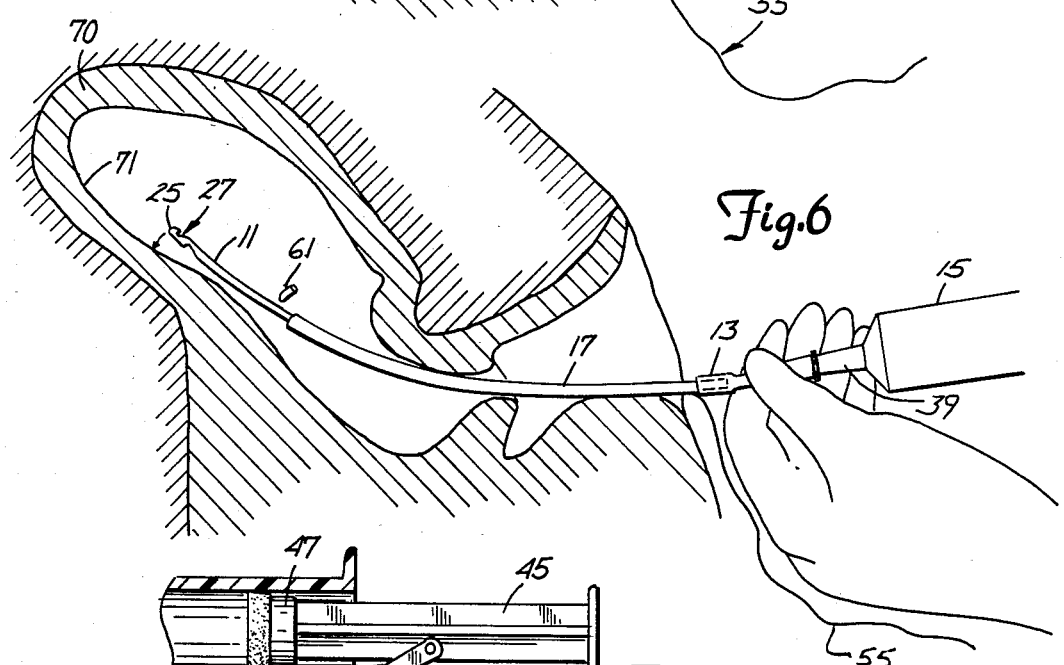
Fig. 6
Fig. 8
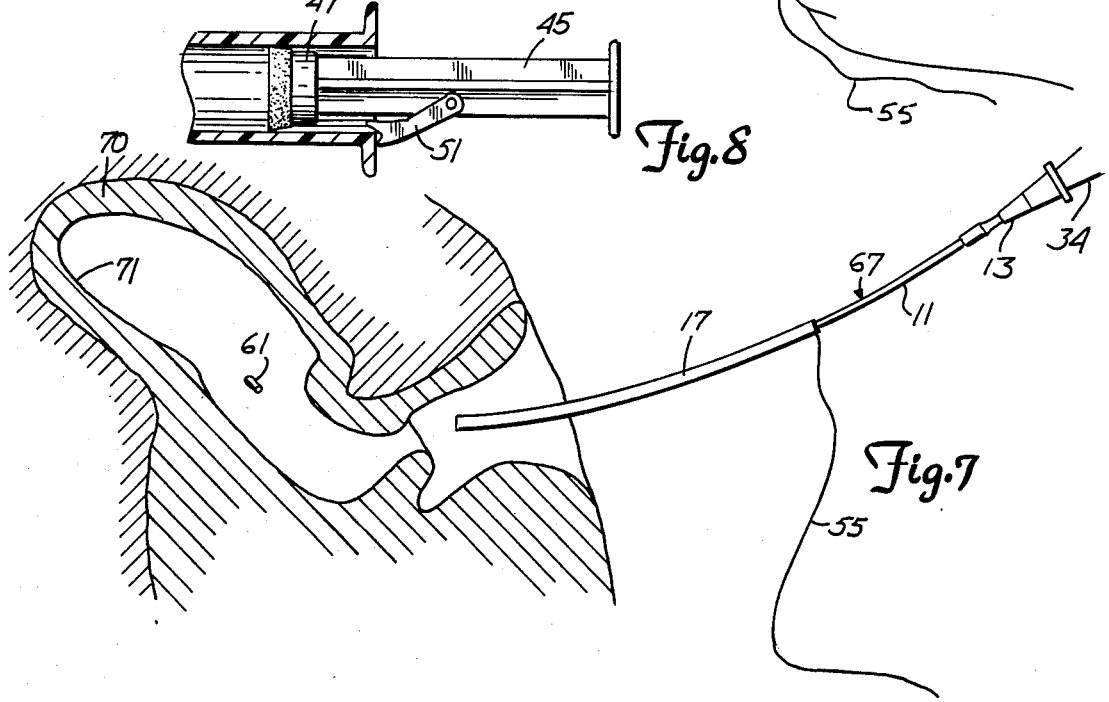
Fig. 7

DEVICE FOR SAMPLING TISSUES AND FLUIDS FROM BODILY CAVITIES

BACKGROUND OF THE INVENTION

1. Field of the Invention

The invention relates to a device and related process for the collection of tissue and fluid specimens from bodily cavities, for example, the human uterus.

2. Description of the Prior Art

Aspirating curettes have been used to remove fluids and/or tissue from bodily cavities. Typically such apparatus has included a curette with a tissue scraping element at its distal end. The distal end of the curette also includes one or more specimen receiving openings leading to a passageway running axially therein. The passageway is commonly connected to a housing containing an outlet for connection to a vacuum source such as a syringe. A screen or other tissue collecting element is placed within the curette passageway or housing. The screen is removably positioned to permit easier examination of the specimen that collects on such screen.

Tissue and/or fluid collection apparatus as described have been heretofore manufactured in a variety of ways. U.S. Pat. No. 3,889,657 to Baumgarten discloses what is referred to as a uterine aspirating curette having a removable, tapered or conical specimen collection basket. Tissue is collected on the inside of the basket, but it is difficult to see and remove for examination. The uterine aspirating curette has a substantially blunt tip and provides four openings to a passageway running axially through the curette. The device is not designed to be used for anaerobic collection of tissue and fluid specimens. In addition, contamination of the device during insertion into the bodily cavity may occur, causing the specimens collected to be similarly contaminated.

U.S. Pat. No. 4,230,123 to Hawkins, Jr. discloses a needle sheath complex having a probe cannula with a stylus slidably mounted therein, such that the stylus substantially fills the probe cannula. The stylus projects from the end of the probe cannula such that a sharp end of the stylus is exposed. Upon location of a target, the stylus is removed from the probe cannula and a syringe is attached to draw a sample of fluid. The device does not have shields or covers for preventing contamination of the sample. Also, the collection process is very tedious and time consuming, and is not designed to be used for the anaerobic collection of tissue and fluid samples.

U.S. Pat. No. 4,311,140 to Bridgman discloses a vacuum curette having an improved curetting opening. The distal portion of the curette has at least a pair of tip openings opposed to one another. One of these openings has a semi-circular cross section, while the other has a rectangular cross section and is designed to macerate tissue for collection.

U.S. Pat. No. 4,338,952 to Augros discloses a device for taking samples of endometrium comprising a rod, a tube and at least one scraper element fixed at the end of the rod. The scraper element is designed to be retracted within the tube. Tissue collection occurs on the scraper element and the sample is then removed for examination. The device does not use a vacuum for the collection of tissue samples and cannot be used for fluid collection. Also, the device is unable to anaerobically collect tissue samples.

U.S. Pat. No. 4,393,879 to Milgrom discloses a tissue collecting apparatus comprising a curette having a tissue scraping element at its distal end. A proximal end of the curette is attached to a housing having an outlet adapted to be connected to a source of vacuum. Within the housing is an obliquely mounted tissue collecting screen. The use of such a tissue collecting screen is not conducive to anaerobic tissue and fluid sampling. Also, the specimen may become contaminated due to the lack of any contamination preventing shield or cover.

U.S. Pat. No. 4,396,022 to Marx discloses an endometrial tissue sampling apparatus comprising a sheath with a path dilating pilot obturator adapted to slide therein. Following insertion, the obturator is removed from the sheath and a syringe is attached to the outer end of the sheath. The syringe is then used to form a vacuum to draw the endometrium against the cutting edge of a scraping tip held on the sheath to remove tissue specimens which pass through the sheath into the syringe. The use of the syringe as a specimen collecting device does not permit discovery of anaerobic pathogens, as the specimen must be expelled into a container for examination, thus exposing it to air. Such exposure to air is toxic to strict anaerobes.

The prior art lacks the capability of effectively collecting anaerobic tissue and fluid samples.

Uterine infections are usually mixed, including organisms from the groups of aerobic, anaerobic, and facultatively anaerobic organisms. Aerobic organisms utilize oxygen for growth; lack of oxygen may result in cessation of growth, but not death. Facultative anaerobes can grow in the presence or absence of oxygen. Strict anaerobes, however, cannot tolerate any exposure to oxygen, which is fatally toxic to them. Therefore, the usual sampling devices will fail to collect viable anaerobes. Since successful selection of proper therapeutic agents requires culture and identification of all of the pathogenic organisms, failure of treatment may occur, with resulting prolonged morbidity, mortality or sterility.

In the case of postpartum infection, the baby may also have acquired the infection before or during birth. Diagnosis of the mother's infection provides indication of proper therapy for the baby and the diagnosis may be made more rapidly because of the larger inoculum of the maternal sample. Particularly in the case of Chlamydia trachomatis, which infects the baby's cornea and lungs, causing blindness and pneumonia, respectively, identification of pathogens in the maternal sample is as desirable as direct sampling of the baby.

Chlamydia trachomatis is an increasingly common cause of pelvic inflammatory disease (PID). It is an unusual bacterial pathogen in that it grows within the cell and is shed into the surrounding fluids. It can be found in extracellular fluid and as an intracellular organism. Since it is a fastidious intracellular parasite, it may be diagnosed either by culture or by cytologic examination of the tissue sample as well as the fluid from the syringe. The extracellular organisms are often present and may even be dead. Taking of a tissue sample, with the organisms inside the cells, can assure the pathologist of the correct identification of this pathogen. Once diagnosed, the pathogen can be treated with specific antibiotics. Broad spectrum antibiotics commonly used for treating pelvic infections may be ineffective against Chlamydia.

Another difficulty attendant with prior art aspirating curettes is the lack of a structure to effectively prevent contamination. Specimen contamination may occur when the device is introduced to the bodily cavity. Thus, a tissue and/or fluid specimen may contain samples from unwanted or unaffected areas. An additional disadvantage in many prior devices is the use of expensive tissue collecting screens.

SUMMARY OF THE INVENTION

The present invention comprises an aspirating curette or catheter for anaerobically collecting tissue and fluid specimens from a bodily cavity which are protected from contamination and a process for operating the curette. Contamination is prevented by sealing the interior of the curette from the environment during insertion of the device into the bodily cavity.

Anaerobic specimen collection is achieved in that the curette of the present invention may be aspirated while collecting specimens and operated to insure the specimen is not exposed to oxygen until it has been analyzed. The curette has a distal end, adapted for insertion into a bodily cavity, and has at least one notch in its side to provide an opening that has edges to facilitate a scraping action to loosen tissue. The notch also provides an opening to a passageway running axially along the interior of the curette which is used for tissue and fluid specimen collection.

The base or proximal end of the aspirating curette is attached to a vacuum producing device such as a syringe, so that a vacuum may be formed in the passageway of the curette to facilitate the tissue and fluid sampling.

The aspirating curette as shown is encased in a protective sleeve including a removable distal end cap covering and enclosing the distal end of the curette and the protective sleeve to insure maintaining the distal end of the curette contamination free.

The protective sleeve is shorter than the curette and when assembled there is a space between the base or proximal end of the curette and the base or proximal end of the sleeve. A stop is provided to prevent the protective sleeve from accidentally sliding relative to the curette during insertion. The stop as shown is a split sleeve or tube that slips over the curette and against which the base or proximal end of the protective sleeve will abut. The stop is removed when the curette and protective sleeve are fully inserted to permit the curette to be moved farther inwardly relative to the protective sleeve to force the cap off the protective sleeve and expose the notch for sampling.

The curette is retracted into the protective sleeve after sampling and the curette and protective sleeve are removed with the curette thereby protected from contamination and closed to prevent oxygen from contacting the specimen. Markings are provided on both the protective sleeve and the curette to aid in proper insertion, extension and retraction of the curette.

BRIEF DESCRIPTION OF THE DRAWINGS

FIG. 1 is a perspective of an aspirating curette and syringe assembly made according to the present invention;

FIG. 2 is a fragmentary enlarged sectional view of the distal end of the curette of the present invention showing a protective sleeve and seal and taken as on line 2—2 in FIG. 1;

FIG. 3 is a cross sectional view taken on line 3—3 in FIG. 1;

FIG. 4 is a side view of the aspirating curette of FIG. 1 as it appears prior to use;

FIG. 5 is a schematic representation of the device of the present invention in position within a bodily cavity immediately following insertion;

FIG. 6 is a view similar to FIG. 5 after the aspirating curette has been pushed through the protective sleeve in a subsequent step of use;

FIG. 7 is a view similar to FIGS. 5 and 6 following removal of the curette from the bodily cavity; and FIG. 8 is a fragmentary sectional view of the outer end of a syringe showing a lock member for the plunger.

DETAILED DESCRIPTION OF THE PREFERRED EMBODIMENTS

A tissue or fluid collecting device made according to the present invention is generally indicated at 10 in FIG. 1. The tissue and fluid collecting device includes a tubular aspirating curette or catheter 11 attached to a connector 13 which in turn is connected to a vacuum producing device such as a syringe 15. The aspirating curette 11 is encased by a tubular protective sleeve 17 and removable, axially slit stop sleeve 19. The protective sleeve 17 is shorter than the curette and the stop sleeve 19 is of suitable length to limit sliding movement of the protective sleeve relative to the curette toward the base end (where connector 13 is attached) when the stop sleeve 19 is positioned on the curette. The protective sleeve 17 is more rigid than sleeve 19, which is fairly flexible to aid in removal. The protective sleeve 17 will supply the requisite rigidity for insertion of the curette-sleeve assembly 18 into a bodily cavity and for manipulation of the curette.

The protective sleeve is sealed with an internal plug 20, and an end cap 21 as shown in FIG. 2. The plug and cap are absorbable. The plug 20 and cap 21 protect the distal end of the aspirating curette from contaminating ambient conditions until the seal is removed.

The aspirating curette 11 is a typical aspirating curette made of a material having the flexible properties of polyethylene. The aspirating curette has a distal end 23 having a rounded tip 25 to avoid excessive trauma to the tissue of the bodily cavity when the curette is used for sampling tissue. The distal end 23 also has at least one notch 27 that defines edges to provide a scraping action sufficient to loosen tissue from the bodily cavity wall. As shown, there are two notches, and each notch forms an opening 29 to a passageway 31 running axially along the interior of the tubular aspirating curette 11. Tissue and fluid specimens from a bodily cavity are collected in the passageway 31 during sampling from a bodily cavity. The aspirating curette 11 has a substantially constant diameter along its length. This permits the protective sleeve to slide over and along the curette.

The aspirating curette 11 has a proximal end 33 that is sealingly attached to a connector 13 at the end of a first portion 32 of the connector 13. A second portion 34 of the connector has a large diameter conical opening for frictionally receiving the tip 39 of syringe 15. The frictional connection provides an air tight seal attachment to facilitate the formation of a vacuum within the passageway 31 of the aspirating curette 11 when the syringe 15 is actuated. The connector 13 can be any desired construction to provide an air tight seal to both the curette 11 and the syringe 15.

As stated, the syringe is attached to the connector 13 by frictionally placing the tip 39 into the conical connector portion 34 to provide an air tight seal so that a vacuum may be formed in the passageway 31 of the aspirating curette 11. The syringe 15 has a cylindrical wall 41 forming a barrel in which a plunger 45 is slidably mounted. The plunger 45 has a head or piston end 47, which provides an air tight seal against the interior surface of wall 41 to permit the formation of a vacuum when the plunger 45 is retracted toward an outer end 49 of the syringe 15. A conventional spring loaded lock tab 51 is pivotally mounted on the plunger 45 and as seen in FIG. 8, will spring out to abut on the end of the syringe barrel to hold the plunger out and thus to hold the vacuum created. This lock is available on commercial syringes.

The protective sleeve 17 in a first position encases a substantial portion of the aspirating curette 11 and overlaps or extends outwardly from the distal portion 23 of the aspirating curette. The protective sleeve 17 is large enough to permit it to slide on the aspirating curette. Scale markings 53 are placed on the protective sleeve 17 to indicate distances from the distal end to permit insertion of the aspirating currette 11, protective sleeve 17, and stop means 19, to a desired depth within a bodily cavity. The protective sleeve 17, is constructed of a nontoxic, somewhat flexible material such as polyethylene and is of size to provide sufficient rigidity for insertion into a bodily cavity.

A retrieval line 55 is attached to the proximal end of protective sleeve 17. The retrieval line 55 is of a length sufficient to extend outside of the bodily cavity in which the curette is inserted. The retrieval line 55 may be used to facilitate the removal of the protective sleeve 17 and the curette from the bodily cavity after use.

The removable stop sleeve 19 is a flexible tube with a slit 57 along its length. The slit 57 permits removal of the stop sleeve 19 after insertion of the curette-sleeve assembly 18, including the stop sleeve 19, into a bodily cavity. The stop sleeve 19, is constructed of a nontoxic material which is flexible enough to permit easy removal. The stop sleeve 19 forms removable stop means which abut the proximal end of protective sleeve 59 and connector 13 to keep the protective sleeve 17 from sliding along the curette toward the proximal end 33 during insertion into a bodily cavity. Following insertion, the stop sleeve 19 is removed, permitting the aspirating curette 11 to slide through the protective sleeve 17 as needed.

A seal 61 is provided at a distal end 65 of the protective sleeve. The seal consists of the absorbable plug 20 which is inserted into the outer or distal end 65 of the protective sleeve, and a gelatin end cap 21 which covers and encloses the distal end 65 of the protective sleeve 17. The plug 20 is constructed of a suitable biocompatible absorbable material such as the product sold under the trademark Gelfoam.

The plug 20 and end cap 21 may be dislodged and ejected from the protective sleeve when the aspirating curette 11 is forcibly slid through the protective sleeve 17, thus exposing the distal portion 23 of the aspirating curette and the edges of notches 27 to walls of a bodily cavity in which the aspirating curette is inserted.

As shown in FIGS. 5, 6 and 7, the aspirating curette 11, protective sleeve 17, and stop sleeve 19, will be inserted into a bodily cavity such as the uterus 70 of a patient, either to a desired depth as estimated by palpation and as indicated by markings 53, or until the cap 21 on the distal end 65 of the protective sleeve 17 engages the fundal wall 71. If inserted until striking the fundal wall, the curette protective sleeve and stop sleeve are then retracted a desired distance as indicated by scale 53. Subsequently, the stop sleeve 19 is removed, permitting the aspirating curette 11 to be slid through the protective sleeve 17 as the protective sleeve is held in place, manually or with line 55, thus displacing the seal 61 made up of plug 20 and cap 21, and exposing the notches 27 as shown in FIG. 6. Fluid in the bodily cavity is then aspirated through the openings 29, provided by the notches 27 into the passageway 31 of the aspirating curette by retracting and locking the plunger 45 of the syringe 15. The plunger 45 of the syringe is left retracted using the lock tab 51. The vacuum tends to draw the fundal wall and the distal tip of the curette together. The protective sleeve 17 does provide sufficient rigidity for manipulating the tip of the curette to position against the fundal wall as well. The aspirating curette 11 is then rotated in order to scrape tissue from the fundal wall with the edges defining the notches 27. The loosened tissue is also aspirated through the openings 29 into the passageway 31 of the aspirating curette 11 where it is retained along with the aspirated fluid.

The vacuum is released by releasing lock tab 51. The curette is thus released from the fundal wall.

Next, the aspirating curette 11 is pulled back or retracted into the protective sleeve 17. The aspirating curette 11 and protective sleeve 17 are then removed as a unit from the bodily cavity with the sleeve 17 encasing the distal end of the curette to prevent contamination and prevent oxygen from contacting the specimen, as shown in FIG. 7. Removal of the protective sleeve 17 from the body cavity and through the body passageway is facilitated by the presence of retrieval line 55, if necessary. In most instances, the friction between the protective sleeve and the curette will cause the sleeve to stay in place during removal. The retrieval line 55 preferably has a length sufficient to permit it to extend outside the bodily cavity when the curette and sleeve are fully inserted, so the line 55 can be used to retrieve the protective sleeve if it accidentally slips off the curette when it is in the bodily cavity. Removal is accomplished by simply pulling the syringe 15 and the protective sleeve and curette as a unit away from the body. The curette and specimen are protected from contaminating material in the entrance passageways to the uterus during insertion and removal because, as shown in FIG. 6, the protective sleeve is of length so one end of the sleeve is accessible from outside the vaginal passageway and the other end is still positioned within the uterus and thus not subject to contamination.

After removal of the aspirating curette 11 and protective sleeve 17 from the bodily cavity, the curette is withdrawn from the protective sleeve 17. The aspirating curette 11 may then be cut with sterile scissors at a desired length by referring to the scale 67 marked on the aspirating curette (see FIG. 4). Usually 6 to 8 cm are cut off and dropped into a gassed-out anaerobic culture tube. Aspirated fluid is also injected into the same tube. Then, normal procedures are used for analysis and tests.

This device as shown is particularly adapted to the collection of anaerobic, faultative and intracellular pathogens. It can readily be flushed with a non-oxygen containing gas, such as nitrogen. The tissue sample is never exposed to air. The samples may also be used for cytologic procedures and the diagnosis of aerobic pathogens. An additional advantage is that the device can be inexpensively constructed and discarded after use.

The stop sleeve 19 may be replaced with a shorter collar or a nontoxic clip that clips on to the currette 11 to hold the protective sleeve 17 in place.

Although the present invention has been described with reference to preferred embodiments, workers skilled in the art will recognize that changes may be made in form and detail without departing from the spirit and scope of the invention.

What is claimed is:

1. An apparatus for the collection of tissue and fluid samples from bodily cavities including:
   an aspirating curette comprising a tubular member having a central passageway having a distal end portion adapted for insertion into the bodily cavity, said distal end portion having at least one notch opening to the interior of the tubular member, said notch providing an opening to the passageway which has scraping edges;
   means for attaching a proximal end of said aspirating curette to a vacuum producing means such that a vacuum may be formed in the passageway of the aspirating curette to facilitate the tissue and fluid sampling through the notch;
   a protective sleeve having a length shorter than the length of the aspirating curette encasing the distal portions of said aspirating curette and including means for sealing said protective sleeve at the distal end of the protective sleeve for preventing contamination of the interior of the aspirating curette, said aspirating curette being slidable relative to the protective sleeve between a retracted position within the protective sleeve and a position to force the sealing means from the protective sleeve to expose the notch formed on the aspirating curette for scraping tissue following insertion of the protective cover and curette into a bodily cavity, said curette being retractable into the protective sleeve prior to removal from such bodily cavity in which it is inserted; and
   stop means capable of being rendered ineffective and operable to selectively limit movement of the protective sleeve in direction toward the proximal end of the curette.

2. The apparatus for the collection of tissue and fluid according to claim 1 wherein the outside diameter of said aspirating curette is essentially constant to facilitate sliding relative to said protective sleeve.

3. The apparatus for the collection of tissue and fluid according to claim 1 wherein said aspirating curette has a dome-shaped distal tip and the notch is spaced from the tip.

4. The apparatus for the collection of tissue and fluid according to claim 1 wherein said aspirating curette and said protective sleeve are made of a flexible material.

5. The apparatus for the collection of tissue and fluid according to claim 1 wherein said stop means comprises an elongated tube encasing a portion of a proximal end of said aspirating curette, said elongated tube being slit along its length to allow removal thereof from the aspirating curette after insertion of said aspirating curette and protective sleeve into a bodily cavity.

6. The apparatus for the collection of tissue and fluid according to claim 1 wherein said sealing means comprises means for plugging the distal end of the protective sleeve and means for capping the distal end of the protective sleeve over the plug such that the distal end of the aspirating curette is encased and sealed by said protective sleeve and said capping means.

7. The apparatus for the collection of tissue and fluid according to claim 6 wherein said plug means is made of any biocompatible, absorbable material.

8. The apparatus for the collection of tissue and fluid according to claim 6 wherein said cap means is made of gelatin.

9. The apparatus for the collection of tissue and fluid according to claim 1 wherein at least one of said aspirating curette and protective sleeve are marked in a convenient visual scale to aid in positioning insertion and sampling.

10. The apparatus for the collection of tissue and fluid according to claim 1 and elongated means for retrieving the protective sleeve attached thereto such that the sleeve may be retrieved from the bodily cavity.

11. A process for sampling tissue and fluid from a bodily cavity comprising the steps of:
   a. inserting the distal end of an aspirating curette at least partially encased by a protective sleeve to a desired depth, said curette being tubular and having an opening in the wall thereof adjacent its distal end adapted to permit collecting samples from the bodily cavity into the interior of the curette, the interior of said protective sleeve being initially sealed adjacent the distal end;
   b. restraining movement of the protective sleeve toward a proximal end of the curette during the inserting step by providing a stop to initially limit movement of the protective sleeve toward the proximal end of the curette;
   c. after insertion, disabling the stop, and moving said aspirating curette relative to the protective sleeve for extending the curette outwardly of the distal end of the protective sleeve to expose the opening in the wall of the curette;
   d. aspirating a sample from the bodily cavity into said aspirating curette;
   e. retracting the distal end of the aspirating curette into the protective sleeve while leaving the distal ends of the protective sleeve and the aspirating curette in the bodily cavity; and
   f. removing the aspirating curette and said protective sleeve simultaneously as a unit from the bodily cavity while the distal end of the curette remains retracted into the protective sleeve.

12. The process for the collection of tissue and fluid according to claim 11 wherein the aspirating curette is first inserted to contact a wall of the bodily cavity and is then retracted in the range of 2-4 cm before extending the curette outwardly of the distal end of the protective sleeve.

13. The process of claim 11 wherein the step of aspirating comprises creating a vacuum on the interior of the tubular curette, and wherein the vacuum is released after the aspiration step and before retracting the curette and protective sleeve.

14. An apparatus for the collection of tissue and fluid samples from a bodily cavity having a cavity opening leading to a bodily passageway extending from the exterior to the bodily cavity including:
   a curette comprising a first tubular member having a central curette passageway and having a distal end portion adapted for insertion into a bodily cavity to be sampled, said distal end portion having a curette opening open to the central curette passageway of the tubular member for sampling solids, said first tubular member having a length sufficient to be inserted through the bodily passageway into a bodily cavity such that with the distal end within such bodily cavity a proximal end thereof extends to the exterior of such bodily cavity;

means for attaching a proximal end of said aspirating curette to a vacuum producing means such that a vacuum may be formed in the central curette passageway to facilitate tissue and fluid sampling through the curette opening;

a tubular protective sleeve having a distal end and a proximal end encasing the distal end portions of said first tubular member to form an assembly and including means for sealing a provided sleeve opening of said protective sleeve adjacent the distal end of the protective sleeve for preventing contamination of the central curette passageway of the first tubular member from material entering the sleeve opening at the distal end of the protective sleeve, said first tubular member being slidable relative to the protective sleeve between a retracted position within the protective sleeve and a second position whereby the curette opening is positioned outwardly from the distal end of the protective sleeve within the bodily cavity, the means for sealing being disabled upon positive movement of the first tubular member relative to the protective sleeve to its second position, the first tubular member being slidably retractable into the protective sleeve prior to removal of the assembly from such bodily cavity in which it is inserted; and the first tubular member and protective sleeve assembly having selectively disableable means for restraining the first tubular member and protective sleeve from unintentional axial movement which would extend the first tubular member beyond the protective sleeve, the means for restraining being disabled when the distal ends of the protective sleeve and tubular member are within such bodily cavity to permit the first tubular member to be moved to its second position.

15. The apparatus as specified in claim 14, the means for restraining the first tubular member and protective sleeve from axial movement comprising releasable stop means operative between a proximal end of said protective sleeve and said first tubular member to restrain axial movement of the protective sleeve toward the proximal end of the tubular member.

16. The apparatus of claim 14, wherein the first tubular member has a sufficient length so that the proximal end thereof is manipulable from the exterior of a bodily passageway leading to a bodily cavity being sampled while the distal end remains within such bodily cavity to permit the first tubular member to be retracted into the protective sleeve while the distal end of the first tubular member and protective sleeve both remain completely within such bodily cavity.

* * * * *